United States Patent
Hager, III

(10) Patent No.: US 9,282,808 B1
(45) Date of Patent: Mar. 15, 2016

(54) HANGER ASSEMBLY FOR ATTACHING ARTICLES TO FABRIC

(71) Applicant: Henry C. Hager, III, Prosperity, SC (US)

(72) Inventor: Henry C. Hager, III, Prosperity, SC (US)

(73) Assignee: MRS. J., LLC, Worthington, OH (US)

( * ) Notice: Subject to any disclaimer, the term of this patent is extended or adjusted under 35 U.S.C. 154(b) by 0 days.

(21) Appl. No.: 14/721,449

(22) Filed: May 26, 2015

(51) Int. Cl.
*A45F 5/02* (2006.01)
*F16B 45/00* (2006.01)
*A61F 5/44* (2006.01)

(52) U.S. Cl.
CPC .................. *A45F 5/02* (2013.01); *A61F 5/4408* (2013.01); *F16B 45/00* (2013.01); *Y10T 24/1382* (2015.01); *Y10T 24/1394* (2015.01); *Y10T 24/32* (2015.01); *Y10T 24/3449* (2015.01); *Y10T 24/3485* (2015.01)

(58) Field of Classification Search
CPC . Y10T 24/13; Y10T 24/1382; Y10T 24/1394; Y10T 24/3449; Y10T 24/3485; Y10T 24/32; A45F 5/02; A61F 5/44
See application file for complete search history.

(56) References Cited

U.S. PATENT DOCUMENTS

| | | | |
|---|---|---|---|
| 2,355,705 A * | 8/1944 | Cohn | A47G 25/32 223/85 |
| 3,392,729 A * | 7/1968 | Lenoir | A61J 17/00 24/3.13 |
| 3,913,187 A | 10/1975 | Okuda | |
| 4,189,789 A | 2/1980 | Hofstetter | |
| 5,046,222 A | 9/1991 | Byers et al. | |
| 5,655,271 A | 8/1997 | Maxwell-Trumble et al. | |
| 5,697,661 A | 12/1997 | Robinson, Sr. et al. | |
| 6,007,124 A | 12/1999 | Thies, Jr. | |
| D445,625 S | 7/2001 | Smith | |
| 6,270,485 B1 | 8/2001 | Ekey | |
| 6,295,703 B1 | 10/2001 | Adams et al. | |
| 6,349,844 B1 | 2/2002 | Betras | |
| 6,837,472 B1 | 1/2005 | Beutz | |
| 7,216,404 B1 | 5/2007 | Doyle | |
| 7,292,150 B2 | 11/2007 | Shaw | |
| 8,066,657 B2 | 11/2011 | Frazer | |
| 8,292,860 B1 | 10/2012 | Persichetti et al. | |
| 8,516,613 B2 | 8/2013 | Crites | |

(Continued)

OTHER PUBLICATIONS

Aspen Surgical Product Flyer for 100ML S-Vac Evacuator sterile bulb, Medline, retrieved from http://www.medline.com/ on Apr. 16, 2014.

(Continued)

*Primary Examiner* — Robert J Sandy
(74) *Attorney, Agent, or Firm* — James R. Eley; Claire Patton; Eley Law Firm Co., LPA

(57) ABSTRACT

A hanger assembly includes a mount and an attachment assembly portion extending from a curved portion of the mount. The mount is configured to receive and slidingly retain one or more articles. The attachment assembly portion includes a base and a clamp and is configured to selectively attach to the fabric. The base is configured to receive a portion of the fabric and the clamp. The clamp is configured for removable captive engagement with the base for selectively securing the fabric to the base when engaged. The base is configured to selectively attach to the fabric by engagement of the clamp with a rear side of the base. At least one article is slidably mounted on the curved portion of the mount to retain the article in proximity to the fabric when the base and clamp are engaged.

20 Claims, 6 Drawing Sheets

(56) References Cited

U.S. PATENT DOCUMENTS

| | | | |
|---|---|---|---|
| 2002/0170147 A1* | 11/2002 | Heller | A45F 5/02 24/3.3 |
| 2003/0014844 A1* | 1/2003 | Splane, Jr. | A45F 5/02 24/3.1 |
| 2005/0072820 A1 | 4/2005 | Hardison | |
| 2008/0282441 A1 | 11/2008 | Green | |
| 2008/0294128 A1 | 11/2008 | Richards | |
| 2008/0296325 A1 | 12/2008 | Tepper | |
| 2009/0019671 A1* | 1/2009 | Trullas | A45F 5/02 24/3.3 |
| 2011/0219511 A1 | 9/2011 | Fishbein et al. | |
| 2013/0219667 A1* | 8/2013 | Walczak | A44B 99/00 24/3.1 |

OTHER PUBLICATIONS

"Systems and Accessories for Wound Drainage", Brochure, Zimmer GmbH, Switzerland, May 2012.

"Another type of Need by other Special People in my life", homemade post mastectomy gift ideas, Blog posting from Apr. 3, 2013, Special Needs House, retrieved from http://specialneedshouse.blogspot.com on May 23, 2014.

Pink Pockets product information for post-mastectomy drain holders, retrieved from http://www.pink-pockets.com/ on May 27, 2014.

* cited by examiner

HANGER ASSEMBLY FOR ATTACHING ARTICLES TO FABRIC

FIELD

The present invention relates generally to a hanger assembly for attaching articles to fabric, in particular to hanger assembly having an attachment assembly portion with a base and a clamp configured for removable attachment to fabric.

BACKGROUND

Following many surgeries, patients are required to utilize drainage bottles, bulbs or containers connected by flexible tubes to a wound to remove excess fluid. Typically, several of these drainage containers are required to be supported continuously in close proximity to the patient's body; during sleep as well as during showers or bathing. The drainage containers may be individually fastened by clips, pins or tape to the patient's clothing, skin or bedding. However, as the drainage containers fill and become heavy, it becomes inconvenient to remove and reattach the multiple fasteners several times a day.

Accordingly, there remains a need for a hanger assembly that is configured to hold multiple removable containers or other articles, easily attachable and removable from fabric, and easily hung up in a shower or suspended off other structures separate from the user, as required.

SUMMARY

According to one embodiment a hanger assembly for attaching articles to a fabric includes a mount having a generally curved portion along its longitudinal axis. The mount is configured to receive and slidingly retain one or more articles. An attachment assembly portion extends from the curved portion of the mount and is configured to selectively attach to the fabric. The attachment assembly portion includes a base and a clamp. The base is configured to receive a portion of the fabric and the clamp. The clamp is configured for removable captive engagement by press fitting with the base for selectively securing the fabric to the base when engaged. The base includes a rear side and a front side and is configured to selectively secure the fabric by engagement of the clamp with the rear side of the base. At least one article is slidably mounted on the curved portion of the mount to retain the article in proximity to the fabric when the base and clamp are engaged.

According to another embodiment a hanger assembly for attaching articles to a fabric includes a mount having a generally curved portion along its longitudinal axis. The mount is configured to receive and slidingly retain one or more articles. An attachment assembly portion extends from the curved portion of the mount and is configured to selectively attach to the fabric. The attachment assembly portion includes a base and a clamp. The base is configured to attach magnetically to the clamp. The clamp is configured for removable magnetic engagement with the base for selectively securing the fabric against the base when engaged. The base includes a rear side and a front side and is configured to selectively secure the fabric by engagement of the clamp with the rear side of the base. At least one article is slidably mounted on the curved portion of the mount to retain the article in proximity to the fabric when the base and clamp are engaged.

According to further embodiment of the present invention a method for making a hanger assembly for attaching articles to a fabric includes the step of providing a mount. The mount includes a portion being generally curved along its longitudinal axis. The mount is further configured to receive and slidingly retain one or more articles. The method includes the step of extending an attachment assembly portion from the curved portion of the mount. The attachment assembly portion is configured to selectively attach to the fabric and includes a base and a clamp. The method includes the step of slidably mounting at least one article on the curved portion of the mount. The method further includes the step of configuring the base to receive a portion of the fabric and the clamp and to selectively secure the fabric by engagement of the clamp with a rear side of the base. The method further includes the step of configuring the clamp for removable captive engagement with the base for selectively securing the fabric to the base when engaged and to retain the article in proximity to the fabric when the base and clamp are engaged.

BRIEF DESCRIPTION OF THE DRAWINGS

Further features of the inventive embodiments will become apparent to those skilled in the art to which the embodiments relate from reading the specification and claims with reference to the accompanying drawings, in which:

DETAILED DESCRIPTION

Figure 1:
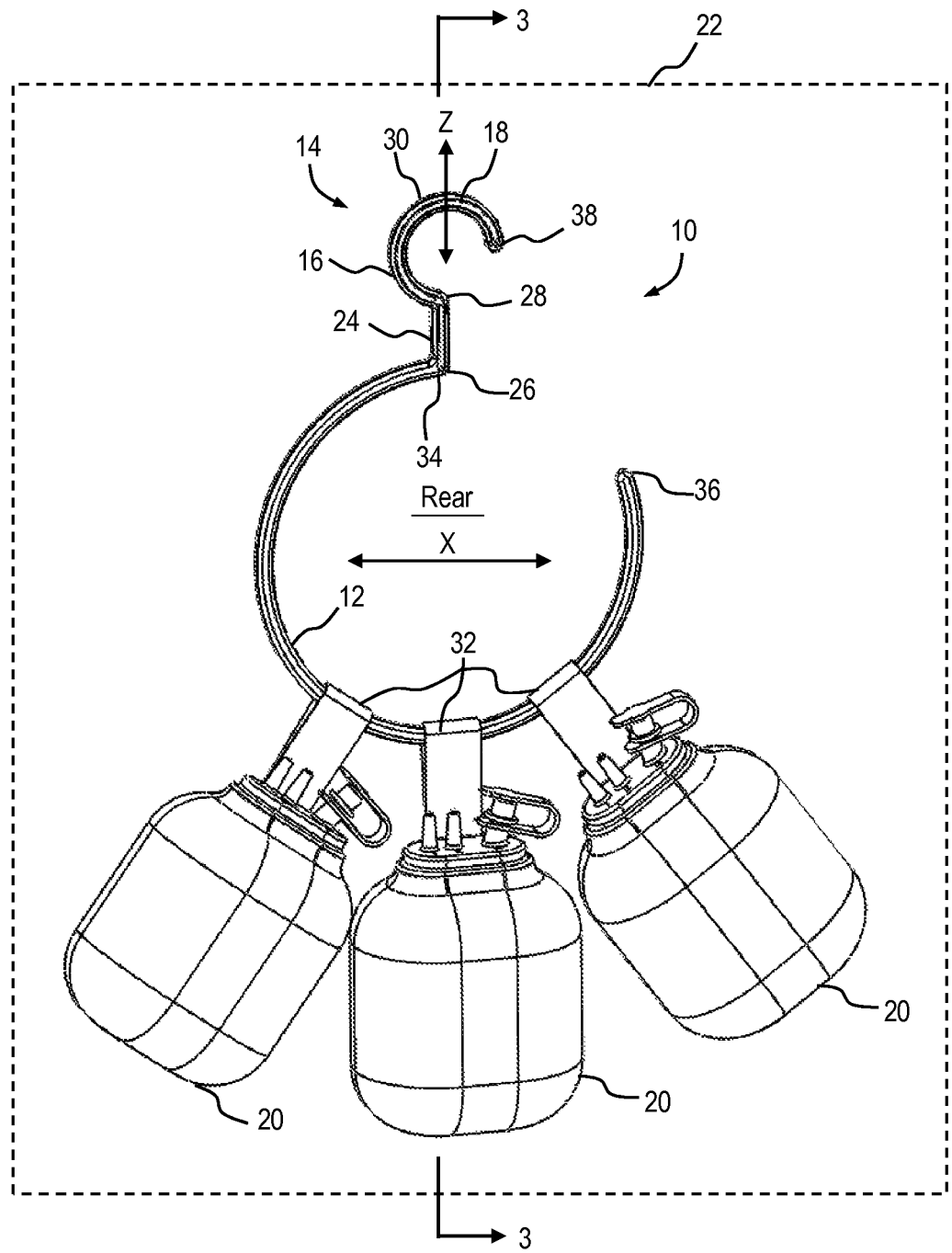
FIG. 1 is a rear elevational view of an assembled hanger assembly with the fabric shown in phantom according to an embodiment of the present invention.

In the discussion that follows, like reference numerals are used to describe like elements in the various figures and embodiments. Furthermore, the elements in the various figures are not necessarily to scale.

The general arrangement of a hanger assembly 10 is shown in FIGS. 1 through 7 according to an embodiment of the present invention. Hanger assembly 10 includes a mount 12 extending from or connected to an attachment assembly 14. Attachment assembly 14 includes a base 16 extending from or connected to mount 12 and a detachable clamp 18. Clamp 18 is configured for removable captive engagement with base 16. Mount 12 is preferably an elongate generally cylindrical rod configured to receive and slidingly retain one or more articles 20. The attachment assembly is configured for selective attachment to a fabric 22 (see FIGS. 3 and 6). Base 16 is configured to receive a portion of fabric 22 and clamp 18. Base 16 is further configured for selectively attaching to fabric 22 by mating engagement of clamp 18 with the base.

Base 16 preferably includes a generally elongate neck 24 with a first end 26 extending from mount 12 and a second end 28 connected to a curved hook 30. Neck 24 serves to space apart hook 30 from mount 12 and to add addition structure for attachment of fabric 22. Alternatively, hook 30 may directly attach to or extend from mount 12. Hook 30 is configured to conveniently attach to or hang suspended from any suitable structure separate from the user, such as, without limitation, a shower head, shower rod, towel rod, hand rod, or mobile IV stand (none shown) as required. Attachment assembly 14 may be utilized both in close-coupled mode for attachment of hanger assembly 10 to clothing or fabric on or adjacent to the user, and in remote mode for attachment to or suspension from structure adjacent to the user via hook 30. When utilized in remote mode, clamp 18 of hanger assembly 10 may or may not be coupled to base 16.

Figure 2:
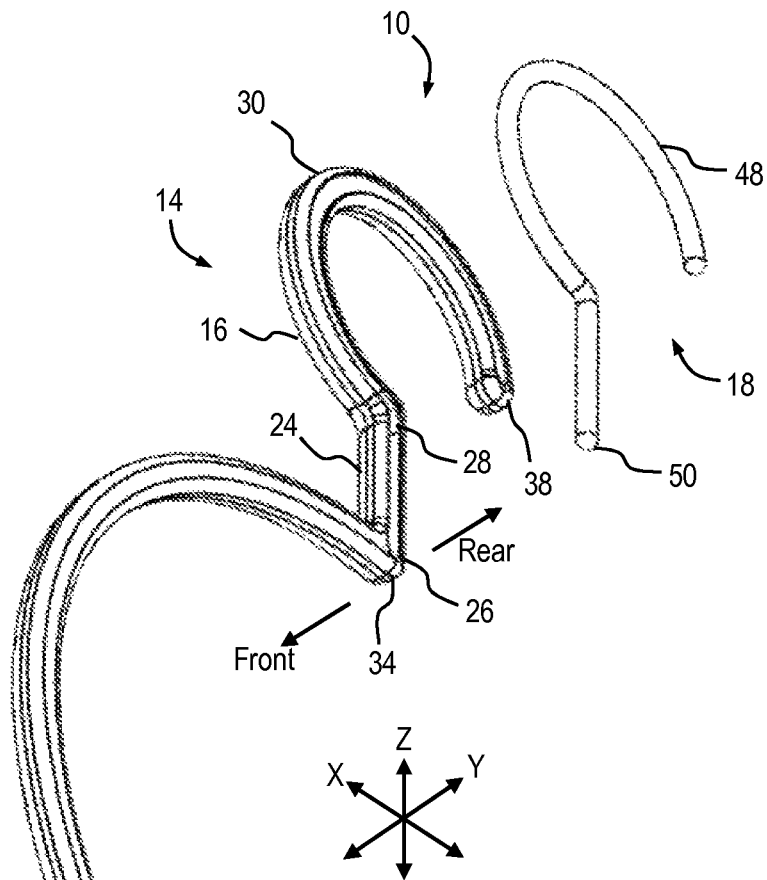
FIG. 2 is an rear perspective exploded view of the hanger assembly of FIG. 1 showing the clamp unassembled and with the articles (drainage reservoirs) and fabric removed.
Figure 2:
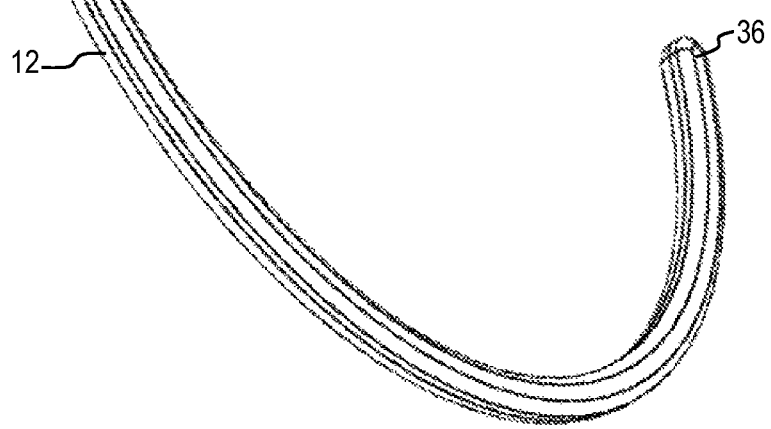
Figure 3:
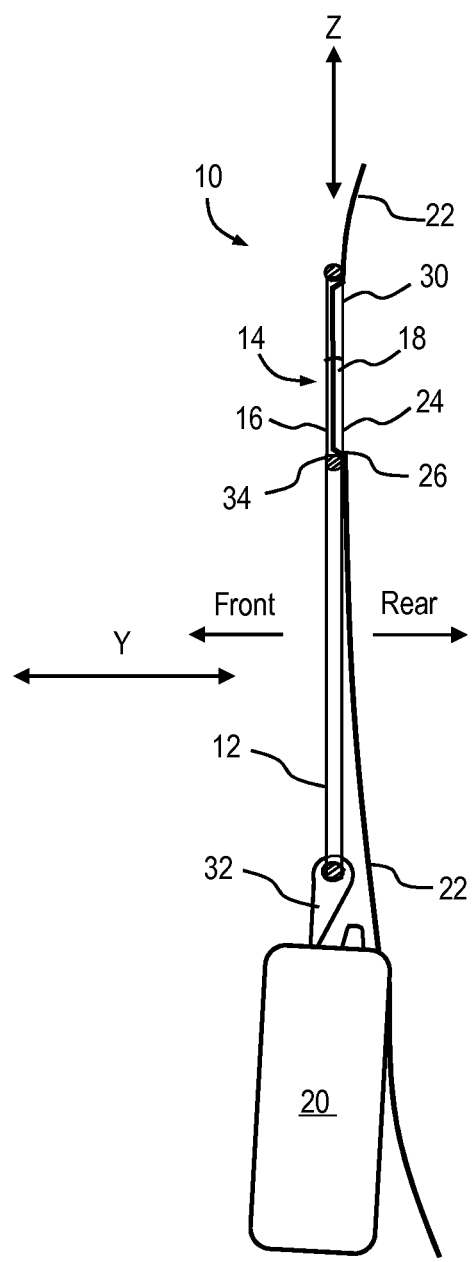
FIG. 3 is a side sectional elevational view of the hanger assembly of FIG. 1 with fabric attached according to an embodiment of the present invention.

Referring to FIGS. 1-3, the elongate shape of hanger assembly 10 is formed preferably with portions symmetrical about a central axis "Z". Hook 30 preferably includes at least a portion formed in a curved, arcuate shape along its longitudinal axis and may be formed in a generally circular arc shape. Other suitable shapes for hook 30 may include, without limitation, oval, egg, oblong, triangular, or teardrop. Mount 12 preferably includes at least a portion formed in a curved, arcuate shape along its longitudinal axis, and may be formed in a generally circular arc shape. This compact shape acts to more evenly balance and distribute of the weight of articles 20 while keeping the articles generally closely adjacent to each other. Other suitable shapes for mount 12 may include, without limitation, oval, egg, oblong, triangular, or teardrop. The central point about which the longitudinal axis of mount 12 curves is generally aligned along the Z axis with the central point about which the longitudinal axis of hook 30 curves. Referring to a side-to-side "X" axis shown in FIG. 1, a longitudinal axis of neck 24 is preferably aligned to a plane formed by the XZ axes, and may be formed as a straight member generally parallel to the Z axis.

Articles 20 may include an opening or loop, such as strap 32, configured to easily slide onto and off of mount 12. Mount 12 may connect or extend from first end 26 of attachment assembly 14 at a proximal end 34 and includes a cantilevered distal end 36. Distal end 36 is configured to receive strap 32, although the strap may also be received by a cantilevered open end 38 of hook 30. Preferably, articles 20 are inserted onto and removed off of hanger assembly 10 at distal end 36 to allow attachment assembly 14 to remain secured to fabric 22 or suspended by adjacent structure. Gravity assists to keep the articles 20 centered about the lower portion of the mount when the hanger assembly 10 is mounted to fabric 22 or to a structure.

Figure 6:
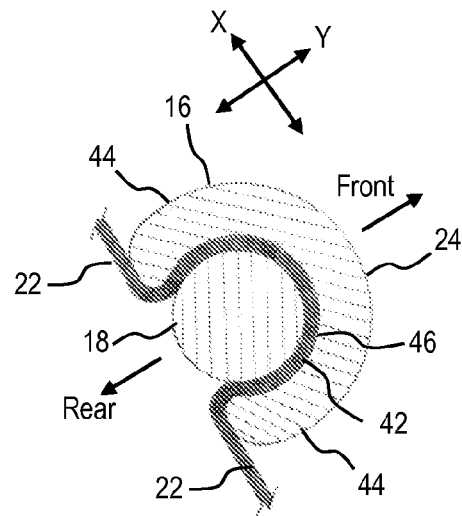
FIG. 6 is a section view of the neck portion of the base and clamp of FIG. 4 captively engaging the fabric according to an embodiment of the present invention.

Referring again to FIGS. 2 and 3, there is a "Y" axis shown for hanger assembly 10, having a front facing side in one direction, and a rear facing side in the other direction, relative to the attachment of fabric 22 and clamp 18. Referring to the "X" axis as shown in FIGS. 1 and 6, the general positioning of hanger assembly 10 and fabric 22 is generally parallel to the plane formed by the XZ axes. When utilized in close-coupled mode, preferably a rear side of base 16 and mount 12 is positioned adjacent a front side of fabric 22, and a front side of clamp 18 is positioned adjacent the rear side of the fabric. Clamp 18 is then urged against an adjacent portion of fabric 22 into base 16 to secure hanger assembly 10 to fabric 22 (see FIG. 6). Thus, when base 16 and clamp 18 are engaged with fabric 22, the articles 20 are retained in proximity to the fabric (FIG. 3).

Referring to FIGS. 4-7, transverse cross-sections of mount 12, clamp 18 and base 16 may be formed generally circular or curved. Preferably, base 16 is formed as an elongate generally cylindrical rod, and the transverse cross-section of base 16 may be generally U-shaped or C-shaped. The transverse cross-section of mount 12 may include one or more of a generally flat portion 40 to assist in stabilizing hanger assembly 10 against the body of a user or other nearby support structure. Preferably, flat portion 40 is disposed generally parallel to the plane formed by the XZ axes, and located on the rear side of mount 12. Alternatively, the cross-sections of mount 12 and base 16 may be formed of any suitable transverse cross-section such as square, oval, rectangular, or polygon. In one embodiment, the geometry of base 16 and clamp 18 may be reversed such that the transverse cross-section of base 16 may be generally circular and the transverse cross-section of clamp 18 may be generally U-shaped or C-shaped. In such case, base 16 would be received by clamp 18.

Figure 4:
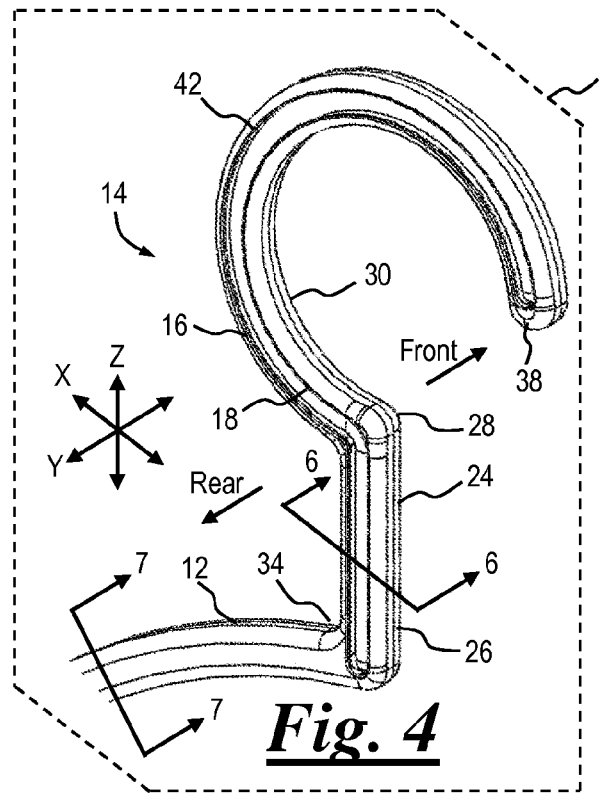
FIG. 4 is an enlarged rear perspective view showing the attachment assembly of FIG. 1 with the fabric shown in phantom.
Figure 5:
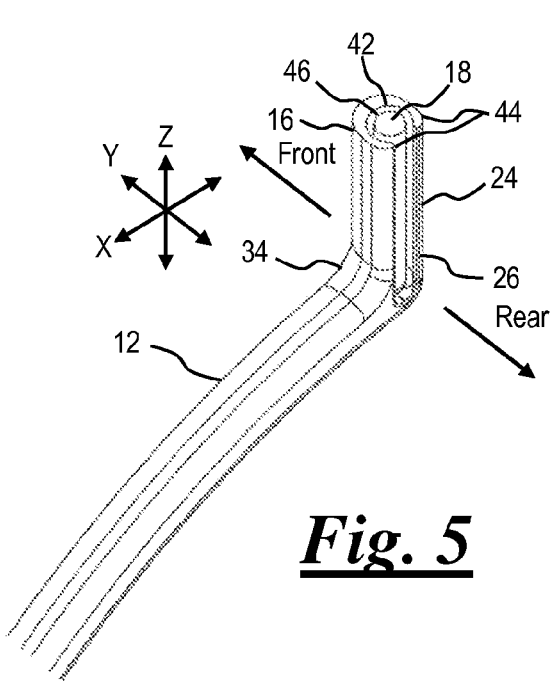
FIG. 5 is a side perspective cut-away view of the neck of the attachment assembly of FIG. 4 showing a portion of the clamp engaged with the channel portion of the base.
Figure 7:
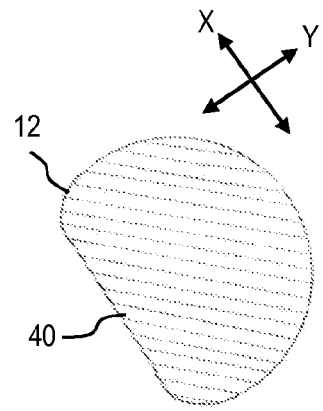
FIG. 7 is a section view of the mount of FIG. 4 according to an embodiment of the present invention.

Referring to FIGS. 4, 5 and 6, base 16 includes a channel 42 configured for receiving and captively engaging clamp 18. Preferably, base 16 includes a pair of opposing lips 44 on either side of channel 42. Channel 42 is configured to maintain a clearance gap 46 when clamp 18 is assembled with base 16, to allow securing of fabric 22 within the gap. Lips 44 are configured to be resilient and to deform as clamp 18 is inserted into channel 42, thus clamping by friction-fit. Alternatively, or in addition, base 16 may be made of a resilient material such that the base is capable of flexing or deforming along its longitudinal axis to allow insertion of clamp 18. The open side of channel 42 is generally parallel to flat portion 40 and located on the rear side of base 16, generally also parallel to fabric 22. Thus, as the open side of channel 42 is located on the rear side of base 16 and generally parallel to fabric 22, clamp 18 is easier to insert into base 16, and less fabric is consumed once clamp 18 is inserted. Alternatively, the open side of channel 42 may be located on a side of base 16 parallel to the YZ plane.

Referring to FIG. 2, clamp 18 is preferably formed as an elongate solid or compressible generally cylindrical rod. Clamp 18 may include one or both of a curved member 48 extending from or connecting to an elongate handle 50. Member 48 preferably includes at least a portion formed in a curved, arcuate shape along its longitudinal axis and may be formed in a generally circular arc shape. Other suitable shapes for member 48 may include, without limitation, oval, egg, oblong, triangular, or teardrop. Clamp 18 is configured to include a shape and size to match and be received by at least a portion of the corresponding channel 42. Preferably, hook 30 and neck 24 are configured to engage curved member 48 and handle 50, respectively, by friction fit with channel 42. As such, once clamp 18 is engaged with base 16, a longitudinal axis of handle 50 is preferably aligned to a plane formed by the XZ axes, and may be formed as a straight member generally parallel to the Z axis. Clamp 18 may be subsequently detached from base 16 by first grasping proximal end 34 of mount 12 and a portion of fabric 22 adjacent to first end 26 of neck 24. Then mount 12 may be gently pulled away and flexed from the front side of fabric 22 at proximal end 34 with sufficient force to overcome the engagement of clamp 18, urging handle 50 out of neck 24. In this state handle 50 may be then be grasped and further separated from hook 30.

In an alternative embodiment, clamp 18 may be a generally closed annular ring, configured to be received by channel 42 of hook 30. In another alternative embodiment, the cross-sections may be reversed such that clamp 18 may be generally closed annular ring including a generally U-shaped or C-shaped profile configured to receive hook 30.

For use in applications where base 16 is attached to fabric 22 proximate to an edge or opening in the fabric, some embodiments of hanger assembly 10 may include a connection feature whereby clamp 18 is tethered or pivotally attached to base 16. Such suitable connection features may include, without limitation, a flexible cord, living hinge, or spring member and may also be configured to generally bias clamp 18 toward base 16. In one embodiment, mount 12 may be rotatably connected to base 16. In another embodiment, mount 12 may be selectively connected to base 16 to allow for all of articles 20 to be easily removed from the user and transported as a single unit.

Although mount 12 and hook 30 are shown as open ended circular arc shapes along their longitudinal axes, either or both may include closure or retention features for additional security in use. Such closure features may include suitable structure such as, without limitation, straps, cords, clips, clamps, hinged or pivoting portions, or extensions. For example, a flexible cord may be attached to distal end 36 of mount 12 at one end and selectively attached to proximal end 34 at the other end, thus preventing articles 20 from inadvertently sliding off the mount. Such retention features may include end caps, bulbs, rings, disks, individual or group clips or clamps. For example, distal end 36 may be inserted into an elastomeric bulb which assists in preventing articles 20 from inadvertently sliding off mount 12. Another example retention feature may be a flexible clip secured onto the strap 32 of the article 20 adjacent distal end 36 to prevent the strap from sliding along mount 12.

Figure 8:
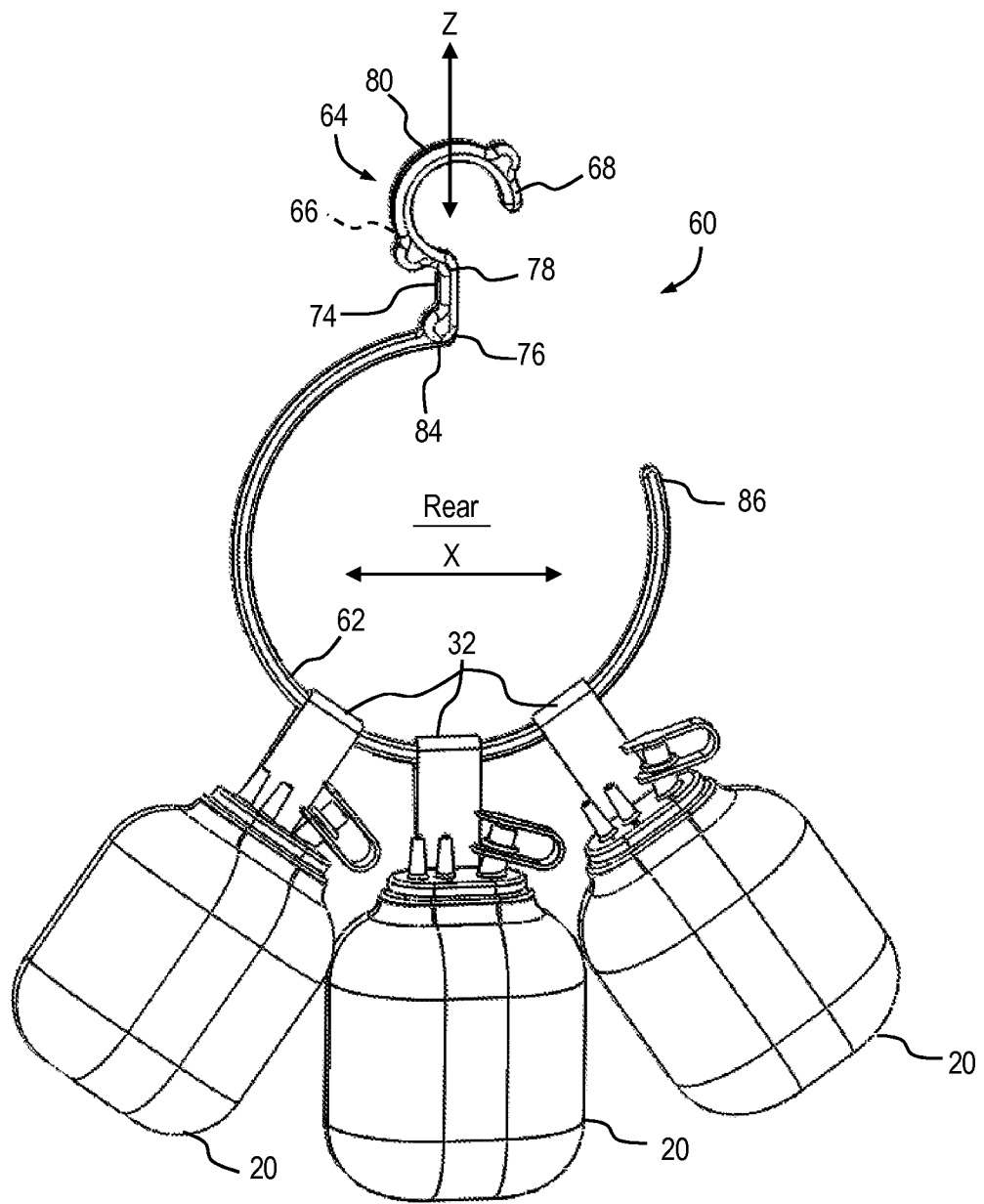
FIG. 8 is a rear elevational view of an assembled hanger assembly without fabric according to an alternative embodiment of the present invention.
Figures 9, 10:
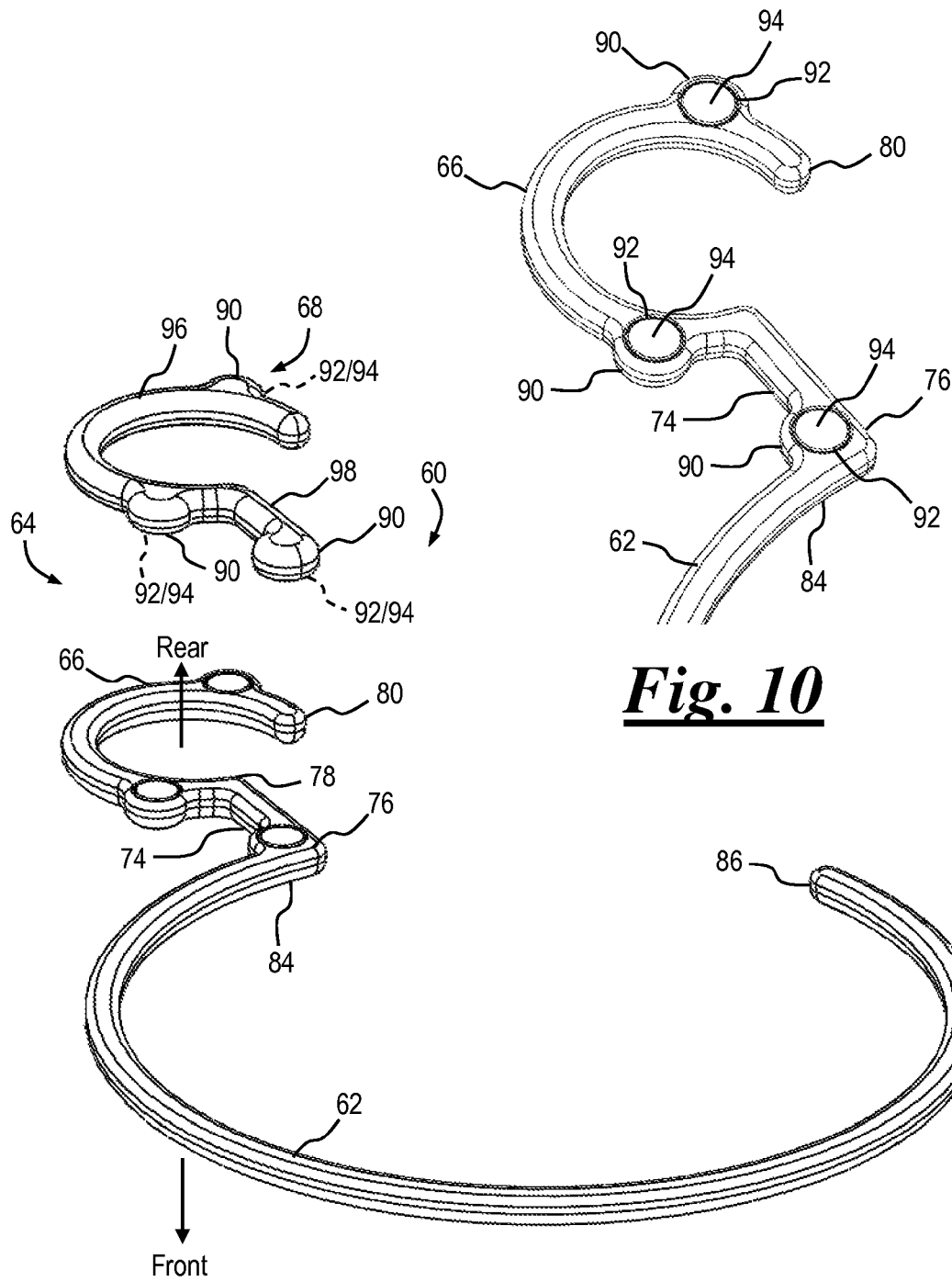
FIG. 9 is an exploded rear perspective view of the hanger assembly of FIG. 8 showing the clamp unassembled and with the articles (drainage reservoirs) removed.
FIG. 10 is an enlarged rear perspective view showing the base of the attachment assembly of FIG. 9.

With reference to FIGS. 8-10, in an alternative embodiment of the present invention a hanger assembly 60 includes a mount 62 and an attachment assembly 64. Attachment assembly 64 includes a base 66 extending from mount 62 and a detachable clamp 68 configured for removable attachment to base 66 by magnetic force. Mount 62 is preferably an elongate generally cylindrical rod configured to receive and slidingly retain one or more articles 20. Clamp 68 is configured to selectively secure a portion of fabric 22 against base 66.

Base 66 preferably includes a generally elongate neck 74 with a first end 76 extending from mount 62 and a second end 78 connected to a curved hook 80. Neck 74 serves to space apart hook 80 from mount 62 and to add addition structure for attachment of fabric 22. Alternatively, hook 80 may directly attach or extend from a proximal end 84 of mount 62. Hook 80 is configured to attach to or hang suspended from any suitable structure separate from the user, similar to hook 30. Attachment assembly 64 may be utilized both in close-coupled mode for attachment of hanger assembly 60 to clothing or fabric on or adjacent to the user, and in remote mode for attachment to or suspension from structure adjacent to the user via hook 80. When utilized in remote mode, clamp 68 of hanger assembly 60 may or may not be secured to base 66.

Similar to hanger assembly 10, the elongate shape of hanger assembly 60 is formed with portions preferably generally symmetrical about an axis "Z" and has similar curvatures along its longitudinal axis. Also similar to hanger assembly 10, straps 32 of articles 20 may be slipped over a distal end 86 of mount 62 and the general positioning of hanger assembly 60 and fabric 22 is generally parallel to a plane formed by the XZ axes. When utilized in close-coupled mode, preferably the rear side of base 66 and mount 62 is positioned adjacent the front side of fabric 22 with the front side of clamp 68 being positioned adjacent the rear side of the fabric. Clamp 68 is then joined to base 66 by magnetic force to secure hanger assembly 60 to fabric 22.

Referring to FIGS. 9 and 10, base 66 and clamp 68 include one or more receptacle portions 90, each receptacle portion 90 having a recess 92. Recess 92 is configured to receive a magnet 94. Magnet 94 may be recessed into recess 92 to provide a flush surface mounting. Magnet 94 may be secured into recess 92 by any suitable feature or method, such as, without limitation, molded-in, pressed-in, or by adhesive. Preferably, magnet 94 is a relatively flat, disk-shaped magnet, but may be of any suitable shape and is formed of such size and suitable material to allow for sufficient magnetic force to be developed. The collective magnetic force should be sufficient to allow clamp 68 to remain engaged to base 66 with fabric 22 secured there-between and up to three fully weighted articles 20 supported by mount 62. Alternatively to a magnet to magnet connection, one or both of base 66 and clamp 68 may include only ferrous metal and be devoid of magnets or may include a combination of ferrous metal and magnets.

Similar to mount 12, the transverse cross-sections of mount 62, base 66 and clamp 68 may include one or more of a generally flat portion 40 to assist in stabilizing hanger assembly 60 against the user or other adjacent structure. Preferably, flat portion 40 is disposed generally parallel to the plane formed by the XZ axes, is located on the rear side of mount 62 and is located on the front side of clamp 68. Similar to clamp 18, clamp 68 may include one or both of a curved member 96 extending or connecting to an elongate handle 98. Member 96 is preferably formed in a curved, arcuate shape along its longitudinal axis, and may be a generally circular arc shape. Member 96 is further configured to include a shape and size to match and align as a mirror image of at least a portion of the corresponding base 66. Clamp 88 may subsequently be detached from base 66 by grasping hook 80 and the clamp. Then clamp 88 may be gently urged away from base 66 with sufficient force to overcome the magnetic engagement of clamp 18, allowing the base to be moved away from fabric 22.

In some embodiments features of attachment assemblies 14 and 64 may be combined to provide both a magnetic and structurally interconnecting clamping of fabric 22. For example, clamp 18 may include ferrous material that is magnetically attracted to additional magnets recessed into base 16. Similar to hanger assembly 10 some embodiments of hanger assembly 60 may include a connection feature whereby clamp 68 is tethered or pivotally attached to base 66. Further similar to hanger assembly 10, either or both of mount 62 and hook 80 may include closure or retention features for additional security during use.

Hanger assemblies 10, 60 may be formed by any suitable process, such as, without limitation, injection molding, machining, casting, extrusion or 3D printing. Hanger assemblies 10, 60 may be formed of suitable metallic or non-metallic materials, such as, without limitation, plastic, aluminum, composites, or wood, or combinations thereof and may include flexible or elastomeric material. Hanger assemblies 10, 60 may be finished in any conventional manner such as painting, coating, plating, molded-in colors and decorative features or may be left unfinished. Preferably, mounts 12, 62 with bases 16, 66, respectively are formed together as a single, unitary piece of plastic and clamps 18 and 68 are formed as single, unitary pieces of metal but may be formed of separate pieces connected by suitable devices or methods, such as, without limitation, welding, pivots, fasteners or adhesive.

In some embodiments the elongate shape of mounts 12, 62 are formed with an interior radius of about 3 to 3.5 inches, necks 24, 74 are formed to be about 1 to 1.5 inches in length and the elongate shape of hooks 30, 80 are formed with an interior radius of about 0.75 to 1 inch, although in other embodiments other sizes or configurations may be used.

Hanger assemblies 10, 60 may be utilized during surgery recovery, athletic activities or other applications to give the user a storage device alternative to pockets, waist pouches, belts, harnesses, slings, bags or purses. Articles 20 may be any suitable weighted item, such as, without limitation, drainage bottles, drink bottles, snack containers, keys, wallets, cell phones or other electronic devices, medication containers or lotion bottles. In one embodiment, articles 20 may be Jackson-Pratt™ drainage bulbs or spring reservoirs such as those made by Cardinal Health, of McGaw Park, Ill. Hanger assemblies 10, 60 may be attached by clamping to a hospital gown such that mounts 12, 62 with articles 20 hangs suspended on the front side of the gown, with individual drainage tubes being routed to wound sites on the user on or proximate the rear side of the gown. When the articles 20 need emptied, they may be disconnected from the drainage tubes and slid to distal ends 36, 86 for easy removal from mounts 12, 62. Once emptied, articles 20 may be easily slid back onto mounts 12, 62 and the drainage tubes reconnected. Thus, the maintenance of the articles 20 may be performed while hanger assemblies 10, 60 remain attached to the user's clothing or bedding.

Fabric 22 may be any suitable material such as, without limitation, a hospital gown, bedding, towel, household robe, or other article of clothing, non-woven fabric, paper product or any other suitable material that may be selectively secured in the attachment assembly of the hanger assemblies 10, 60.

While this invention has been shown and described with respect to detailed embodiments thereof, it will be understood by those skilled in the art that changes in form and detail thereof may be made without departing from the scope of the claims of the inventions.

What is claimed is:

1. A hanger assembly for attaching articles to a fabric, comprising:
   a mount, the mount including a curved portion along its longitudinal axis, the mount further being configured to receive and slidingly retain one or more articles therefrom; and
   an attachment assembly portion extending from the curved portion of the mount, the attachment assembly portion being configured to selectively attach to the fabric, the attachment assembly portion including:
   a base and a clamp, the base including a hook spaced apart from the mount by a neck, the base being configured to receive a portion of the fabric and the clamp, the clamp being configured for removable captive engagement with the base for selectively securing the fabric to the base when engaged;
   the base including a rear side and a front side, whereby the base is configured to selectively attach to the fabric by engagement of the clamp with the rear side of the base; and
   at least one article being slidably mounted on the curved portion of the mount to retain the article in proximity to the fabric when the base and clamp are engaged.

2. The hanger assembly of claim 1, wherein the mount has a circular arc shape portion along its longitudinal axis.

3. The hanger assembly of claim 1, wherein the attachment assembly portion includes a curved portion along its longitudinal axis and is configured for suspending the hanger assembly from an adjacent structure.

4. The hanger assembly of claim 3, wherein the attachment assembly portion includes a circular arc shape portion along its longitudinal axis.

5. The hanger assembly of claim 1, wherein either of the mount, base and clamp comprise a cylindrical rod.

6. The hanger assembly of claim 1, wherein the mount includes a cantilevered distal end.

7. The hanger assembly of claim 1, wherein the clamp includes a cantilevered open end.

8. The hanger assembly of claim 1, wherein a transverse cross-section of the clamp is generally circular.

9. The hanger assembly of claim 1, wherein a transverse cross-section of the base is one of a U-shape and a C-shape.

10. The hanger assembly of claim 1, wherein the clamp includes a curved member extending from an elongate handle.

11. The hanger assembly of claim 1, wherein the base is configured to engage the clamp by friction fit.

12. The hanger assembly of claim 1, wherein the at least one article is a wound drainage bottle.

13. The hanger assembly of claim 1, wherein the at least one article includes a plurality of articles.

14. A hanger assembly for attaching articles to a fabric, comprising:
   a mount, the mount including a portion being curved along its longitudinal axis, the mount further being configured to receive and slidingly retain one or more articles therefrom; and
   an attachment assembly portion extending from the curved portion of the mount, the attachment assembly portion being configured to selectively attach to the fabric, the attachment assembly portion including:
   a base and a clamp, the base including a hook spaced apart from the mount by a neck, the base being configured to attach magnetically to the clamp, the clamp being configured for removable magnetic engagement with the base for selectively securing the fabric against the base when engaged;
   the base including a rear side and a front side, whereby the base is configured to selectively attach to the fabric by engagement of the clamp with the rear side of the base; and
   at least one article being slidably mounted on the curved portion of the mount to retain the article in proximity to the fabric when the base and clamp are engaged.

15. The hanger assembly of claim 14, wherein the mount has a circular arc shape portion along its longitudinal axis.

16. The hanger assembly of claim 14, wherein the clamp includes a curved member extending from an elongate handle.

17. The hanger assembly of claim 14, wherein either of the base and the clamp further include at least one of a recessed magnet.

18. A method for making a hanger assembly for attaching articles to a fabric, comprising the steps of:
   providing a mount including a portion being curved along its longitudinal axis, the mount further being configured to receive and slidingly retain one or more articles therefrom;
   extending an attachment assembly portion from the curved portion of the mount, the attachment assembly portion being configured to selectively attach to the fabric, the attachment assembly portion including a base and an attachment feature, the base including a hook spaced apart from the mount by a neck;
   slidably mounting at least one article on the curved portion of the mount;

configuring the base to selectively attach to the fabric by engagement of the attachment feature with a rear side of the base; and configuring the attachment feature for removable engagement with the base for selectively securing the fabric to the base when engaged and to retain the article in proximity to the fabric when the base and attachment feature are engaged.

19. The method of claim 18, wherein the mount includes a cantilevered distal end.

20. The method of claim 18, wherein the attachment feature includes a cantilevered open end.

* * * * *